(12) United States Patent
Castillo et al.

(10) Patent No.: US 7,205,125 B2
(45) Date of Patent: Apr. 17, 2007

(54) MIXED VIRUS-LIKE PARTICLES

(75) Inventors: Jose Antonio Castillo, Rixensart (BE); Michel Olivier Simon Christian Deschuyteneer, Rixensart (BE)

(73) Assignee: GlaxoSmithKline Biologicals SA, Rixensart (BE)

( * ) Notice: Subject to any disclaimer, the term of this patent is extended or adjusted under 35 U.S.C. 154(b) by 0 days.

(21) Appl. No.: 10/508,242

(22) PCT Filed: Mar. 17, 2003

(86) PCT No.: PCT/EP03/02825

§ 371 (c)(1), (2), (4) Date: Jun. 17, 2005

(87) PCT Pub. No.: WO03/078455

PCT Pub. Date: Sep. 25, 2003

(65) Prior Publication Data

US 2005/0244432 A1 Nov. 3, 2005

(30) Foreign Application Priority Data

Mar. 18, 2002 (GB) ................................. 0206359.2

(51) Int. Cl.
*C12P 12/06* (2006.01)

(52) U.S. Cl. .................. 435/69.1; 435/69.7; 424/204.1

(58) Field of Classification Search ............. 424/204.1; 435/69.1, 69.7, 235.1, 325
See application file for complete search history.

(56) References Cited

U.S. PATENT DOCUMENTS

| 6,123,948 A | * | 9/2000 | Whittle et al. | ............ 424/204.1 |
| 6,245,569 B1 | | 6/2001 | Meyers | ........................ 436/34 |
| 6,908,613 B2 | * | 6/2005 | Wilson et al. | ............ 424/192.1 |

FOREIGN PATENT DOCUMENTS

| WO | WO 99/13056 | * | 3/1999 |
| WO | WO 99/50424 | | 10/1999 |
| WO | WO 00/09699 | | 2/2000 |

OTHER PUBLICATIONS

Buonamassa et al., "Yeast Coexpression of Human Papillomavirus Types 6 and 16 Capsid Proteins". *Virology*, 293(2): 335-344 (2002).
Paintsil et al., "Carboxy Terminus of Bovine Papillomavirus Type-1 L1 Protein is not Required for the Capsid Formation". *Virology*, 223(1): 238-244 (1996).

* cited by examiner

*Primary Examiner*—Ali R. Salimi
(74) *Attorney, Agent, or Firm*—William R. Majarian; Stephen Venetianer; Charles Kinzig

(57) ABSTRACT

The present invention relates to mixed VLPs, and to a process for the production of a mixed VLP, the VLPs comprising L1 proteins from at least 2 different types of human papillomavirus.

22 Claims, 3 Drawing Sheets

31B165c (mixed VLP)

39B122c (HPV 16)

Figure 1:
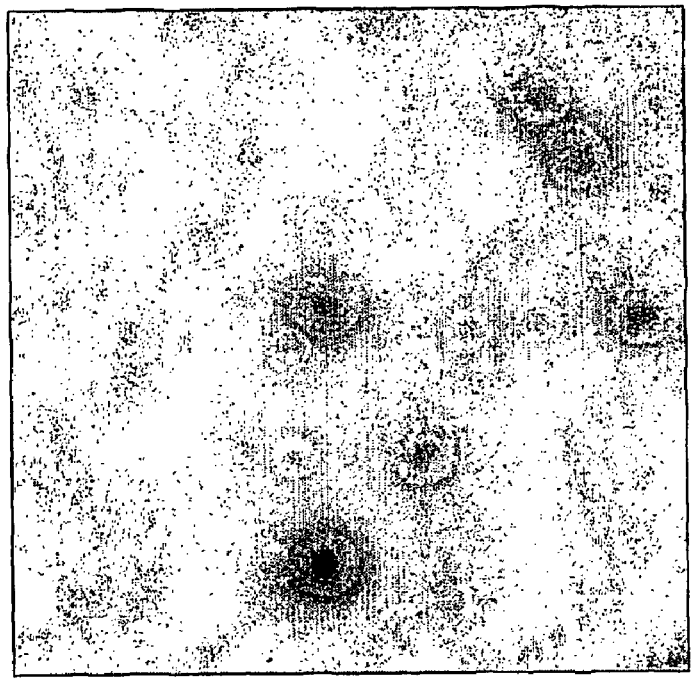
Figure 1:
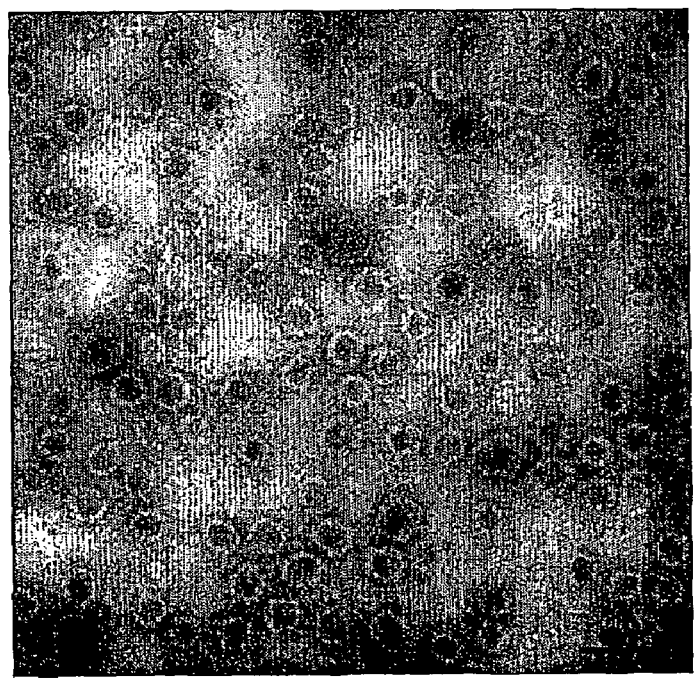

Fig 2 - DLS size measurement of the VLP16-18 Octyl-FT 31B165c
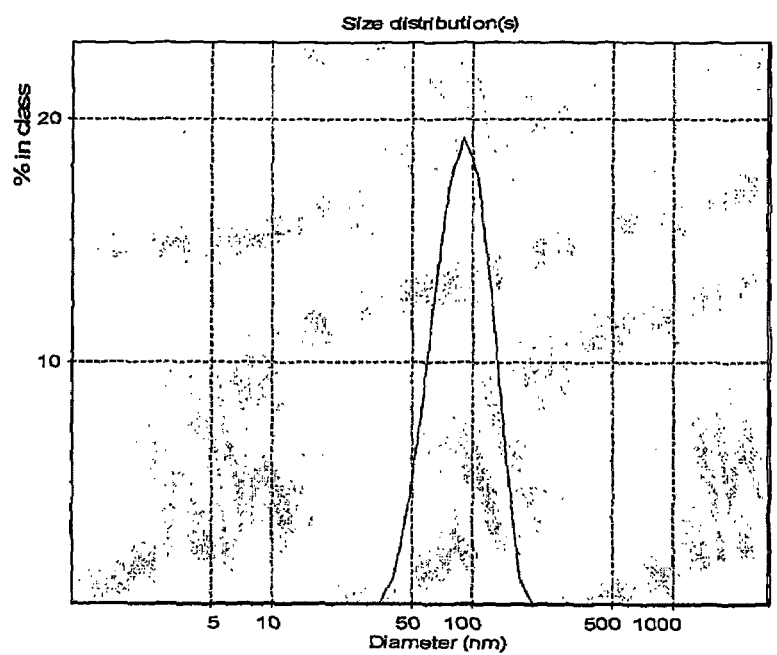

Fig 3 - DLS size measurement of the VLP16-18 Octyl-FT 31B166c
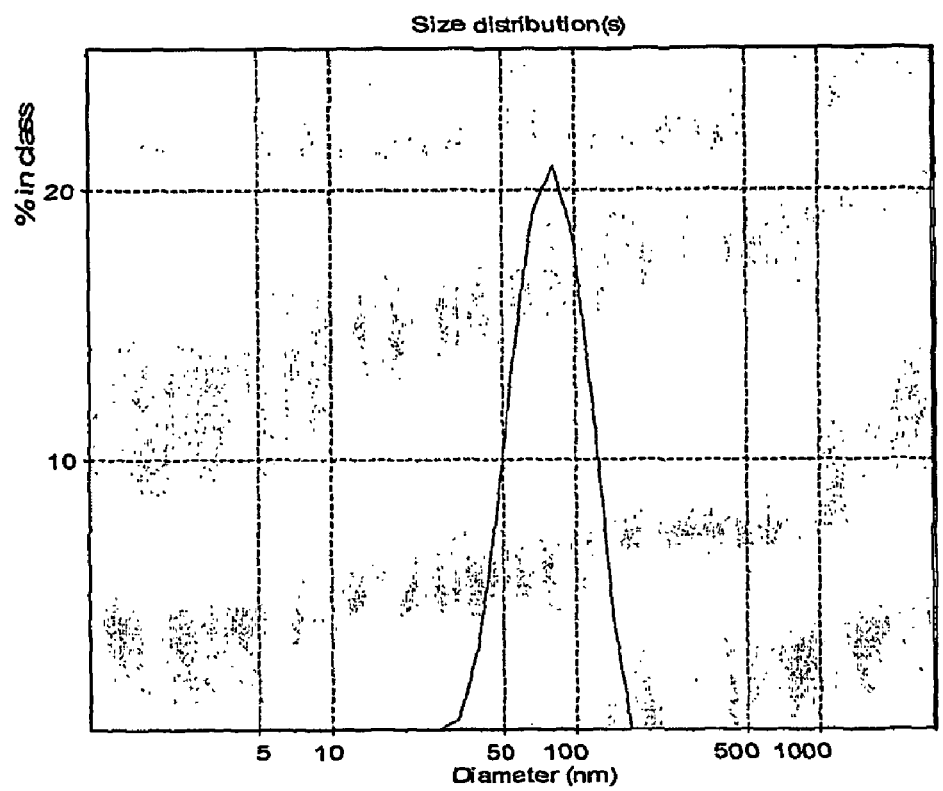

MIXED VIRUS-LIKE PARTICLES

This application is a 371 of International patent application Ser. No. PCT/EP03/02825, filed 17 Mar. 2003, which claims benefit of Great Britain Application No. GB 0206359.2, filed 18 Mar. 2002.

The present invention relates to virus-like particles (VLPs), especially virus-like particles from papilloma viruses (PV).

Introduction

Papillomaviruses are small DNA tumour viruses, which are highly species specific. So far, over 70 individual human papillomavirus (HPV) genotypes have been described. HPVs are generally specific either for the skin (e.g. HPV-1 and -2) or mucosal surfaces (e.g. HPV-6 and -11) and usually cause benign tumours (warts) that persist for several months or years. Such benign tumours may be distressing for the individuals concerned but tend not to be life threatening, with a few exceptions.

Some HPVs are also associated with cancers. The strongest positive association between an HPV and human cancer is that which exists between HPV-16 and HPV-18 and cervical carcinoma Cervical cancer is the most common malignancy in developing countries, with about 500,000 new cases occurring in the world each year. It is now technically feasible to actively combat primary HPV-16 infections, and even established HPV-16-containing cancers, using vaccines. For a review on the prospects for prophylactic and therapeutic vaccination against HPV-16 see Cason J., Clin. Immunother. 1994; 1(4) 293–306 and Hagenesee M. E., Infections in Medicine 1997 14(7) 555–556,559–564.

Other HPVs of particular interest with respect to cancer are serotypes 31,33 and 45, 52, 58, 35, 56, and 59.

Although minor variations do occur, all HPVs genomes described have at least seven early genes, E1 to E8 and two late genes L1 and L2. In addition, an upstream regulatory region harbours the regulatory sequences which appear to control most transcriptional events of the HPV genome.

HPV L1 based vaccines are disclosed in WO94/00152, WO94/20137, WO93/02184 and WO94/05792. Such a vaccine can comprise the L1 antigen as a monomer, a capsomer or a VLP. Methods for the preparation of L1 and L1 VLPs are well known in the art. Such particles may additionally comprise L2 proteins. L2 based vaccines are described for example in WO93/00436. Other HPV vaccines are based on the early proteins, such as E7 or fusion proteins such as L2-E7.

Methods are also known which involve the disassembly and reassembly of VLP's, which can provide for more stable and/or homogeneous papillomavirus VLPs. For example, McCarthy et al, 1998 "Quantitative Disassembly and Reassembly of Human Papillomavirus Type 11 Viruslike Particles in Vitro" J. Virology 72(1):32–41, describes the disassembly and reassembly of recombinant L1 HPV 11 VLPs purified from insect cells in order to obtain a homogeneous preparation of VLP's. WO9913056 and US6245568 also describe disassembly/reassembly processes for making HPV VLPs.

WO00/09699 discloses one specific mosaic VLP between HPV 16 and 6 L1 and L2 VLPs.

The present invention relates to improved VLPs and to a process for the production of such VLPs.

Statement of Invention

In a first aspect the present invention relates to a mixed papillomavirus virus like particle (VLP) comprising 2 or more L1 proteins or functional L1 protein derivatives, the proteins or derivatives being from different papillomavirus genotypes.

The invention also relates to a vaccine comprising mixed papillomavirus VLPs of the invention.

In a further aspect the invention relates to a process for the production of a mixed VLP the process comprising:
  i preparation of an L1 protein or functional L1 protein derivative from at least 2 different papillomavirus genotypes,
  ii mixing the L1 proteins from step 1, if necessary; and
  iii assembly of the proteins or derivatives to produce a mixed VLP.

In particular the invention relates to a process for the production of a mixed VLP, the mixed VLP comprising L1 proteins from at least 2 different types of human papillomavirus, the method comprising the steps of:
  (a) expression of an L1 protein or functional protein derivative from one virus;
  (b) expression of an L1 protein or functional protein derivative from a second virus,
    wherein steps (a) and (b) are carried out separately; and
  (c) mixing of the expressed proteins.

The invention also relates to a mixed VLP obtainable by, or obtained by, the process of the invention.

The invention also relates to a method of treatment of an individual at risk from, or suffering from, a disease related to papillomavirus infection comprising administration of an effective amount of a vaccine comprising a mixed VLP to an individual in need thereof.

The invention also relates to a method for inducing an immune response, the method comprising administration of an effective amount of a vaccine comprising a mixed VLP to an individual in need thereof.

The invention further relates to use of a mixed VLP as defined above in medicine and use of a mixed VLP in the preparation of a medicament for the prevention or treatment of a disease related to papillomavirus infection, such as cervical cancer or genital warts.

DETAILED DESCRIPTION

A 'mixed' papillomavirus VLP, or mixed VLP, is a papilloma virus like particle made up of proteins, or functional derivatives thereof, from more than one papilloma virus genotype. Use of the term 'protein' is hereinafter taken to include functional protein derivatives, unless otherwise indicated or obviously apparent from the context. Functional protein derivatives herein, such as L1 derivatives, are suitably capable of raising an immune response (if necessary, when appropriately adjuvanted), said immune response being capable of recognising a full length protein and/or a VLP consisting of the full length protein and/or the HPV type from which the protein was derived.

Preferably the papilloma virus is a human papilloma virus (HPV).

Preferably a mixed VLP comprises L1 proteins or derivatives from 2, 3, 4 or more different papilloma virus genotypes, most preferably comprising L1 proteins from only 2 different genotypes.

Preferably the mixed VLP does not comprise HPV L2 protein or fragment thereof in the capsid.

Where the papilloma virus is human papilloma virus HPV, then preferably the mixed VLP comprises proteins from HPV genotypes selected from the list of genotypes 1, 2, 3, 4, 5, 6, 7, 8, 9, 11, 12, 14, 15, 16, 17, 18, 19, 20, 21, 22, 23, 24, 25, 26, 27, 28, 29, 31, 33, 34, 35, 36, 37, 38, 39, 42, 43, 44, 45, 51, 52, 56, 58, 59, 66, 68 and 73. Preferably the genotypes are selected from HPV 16, 18, 6, 11, 31, 33, 45, 52, 58, 35, 56, and 59.

Preferably the mixed VLP comprises or consists of L1 proteins or protein fragments from BPV genotypes 16,18, 6 or 11. Preferably the mixed VLP comprises the L1 protein from HPV 16 in combination with the L1 protein from HPV 18, or the L1 protein from HPV 6 in combination with the L1 protein from HPV 11. All combinations of these 4 genotypes are herein explicitly contemplated. Most preferred is a mixed VLP comprising at least the L1 protein from HPV 16.

Preferred L1 derivatives used to form VLPs are truncated L1 proteins. Preferably the truncation removes a nuclear localisation signal. Preferably the truncation is a C terminal truncation. Preferably the C terminal truncation removes less than 50 amino acids, more preferably less than 40 amino acids. Most preferably the C terminal truncation removes 34 amino acids from HPV 16 and 35 amino acids from HPV 18.

VLPs of the invention may also comprise other functional L1 protein derivatives, including mutants of the full length or truncated HPV L1 proteins such as substitution, insertion or internal deletion, mutants. Suitable derivatives also include codon optimised sequences. The L1 protein or derivative may also be a fusion protein, such as the fusion of the L1 protein with L2 or an early protein.

Preferably the L1 proteins in the VLPs of the invention are not in the form of a fusion protein with another L1 protein or part of an L1 protein. Suitably the mixed VLP comprises no L1 protein in the form of a fusion protein.

The L1 protein or functional protein derivative is suitably able to form a VLP and appropriate derivatives can be assessed by analysis of VLP formation. VLP formation may be readily assessed by the person skilled in the art, using for example electron microscopy to assess VLP morphology or dynamic laser light scattering to measure VLP size and polydispersity. Preferably the polydispersity of the VLPs is less than 0.15, most preferably less than 0.1 and more preferably less than 0.8 when measured using a Malvern Zetasizer 3000HS under conditions as described herein.

The invention contemplates combinations of mixed VLPs. By way of example, a composition might comprise an HPV 16 and HPV 18 mixed VLP in combination with an HPV 11 and HPV 6 mixed VLP. Such a combination is useful in the prevention of genital warts and cancer (as disclosed in, for example, WO0035478, incorporated herein by reference). Other preferred combinations include HPV 16 and HPV 18 mixed VLPs in combination with VLPs or mixed VLPs comprising proteins derived from one or more of HPV 31, 33, 45, 52, 58, 35, 56, and 59. Such combinations are suitable for prevention of cancer.

A preferred process for mixed VLP production comprises preparation of VLP L1 proteins from different papillomavirus genotypes, mixing the VLP protein constituents (where necessary) and assembly of the protein constituents to produce mixed VLPs. Where additional antigens are used, these can be added at any appropriate stage.

In a most preferred process, L1 proteins from different HPV genotypes are expressed separately from one another and then combined to form mixed VLPs under suitable conditions. Co-expression of L1 proteins within the same cell is not generally preferred. For example, L1 proteins may be expressed in independent expression systems prior to mixing. The separable nature of the preferred process is such that the ratios of the components of the mixed VLP can be adjusted to achieve optimal VLP formation and/or immunogenicity for the L1 species within the VLP. This may be different to that which can be obtained by co-expression of L1 proteins within the same cell such that mixed VLPs spontaneously form, and the ratio of different L1 proteins cannot be otherwise adjusted. The present invention thus also relates to a mixed VLP wherein the ratio of different L1 species within the mixed VLP has been optimised for VLP formation and/or immunogenicity.

Preparation of L1 proteins suitably comprises expression of L1 proteins from DNA vectors in an appropriate host cell. Preferably the VLPs are prepared from insect cells, for example Sf9 or Hi-5 cells, although any suitable cells such as *E. coli* or yeast cells, for example, *S. cerevisiae S. pombe* or *Pichia* sp. may also be used.

The L1 proteins may be in the form of a crude extract, be partially purified or purified prior to mixing. Preferably the proteins are at least partially purified before being combined. Optionally, further purification of the mixed VLPs may be carried out after VLP assembly.

Purification suitably includes one or more of the steps of anion exchange chromatography (Di methyl amino ethyl—DMAE), anion exchange chromatography (tri methyl amino ethyl—TMAE), hydroxyapatite chromatography, filtration such as nanometric filtration or ultrafiltration, or hydrophobic interaction chromatography. Preferably at least one anion exchange step is performed during purification, and more preferably 2 anion exchange steps are used. Preferably at least one anion exchange purification step is performed prior to mixing the proteins. Optionally an UV viral inactivation step may be included.

In one embodiment the mixed VLPs may be made by disassembly of 2 or more different VLPs, followed by combination of the disassembled VLP components at any suitable point prior to reassembly. This approach is suitable when VLPs spontaneously form when the L1 protein is expressed, for example, when there is L1 expression in yeast strains.

Where the expression of the L1 protein does not lead to spontaneous VLP formation, preparations of L1 proteins or capsomers may be combined before assembly into VLPs.

Production of papilloma virus VLPs is well known in the art (see for example WO9531532, WO9615247, WO00/09671 and U.S. Pat. No. 5,888,526 the whole contents of which are incorporated herein by reference). Disassembly-reassembly approaches for VLP production are also well known, and are disclosed in, for example, WO0057906 WO9913056 and U.S. Pat. No. 6,245,568 the whole contents of which are incorporated herein by reference.

Assembly of VLPs is generally achieved by removal of a reducing agent. As such, in the present invention, the mixing of proteins to form the mixed VLPs of the invention preferably takes place prior to the removal of a reducing agent from the mixture of proteins. Preferably the process of the invention comprises the step of mixed VLP formation from a mixture of dissociated L1 proteins by removal of a reducing agent from the mixture under conditions that allow VLPs to form.

Preferably the reassembly process results from removal of a reducing agent such as mercaptoethanol.

It is, however, known that VLP formation is dependent upon pH, metal ions and salinity as well as the presence of a reducing agent. As such, under certain circumstances, it may be envisaged that VLPs might form in the presence of a reducing agent. It is only important to the invention that mixing of the proteins from different genotypes occurs prior to the change in environmental condition that allows the VLPs to form, whether this is pH, metal ions, salinity, reducing environment or combination of these.

Generally the components of the VLPs of the invention are mixed in the proportions in which they are desired in the final mixed VLP. For example, a mixture of the same amount of a partially purified L1 protein from HPV 16 and HPV 18 provides a mixed VLP with approximately equal amounts of each protein.

Vaccine solutions comprising mixed VLPs may be stabilised by compositions known in the art, such as those of WO 98/44944, WO0045841, incorporated herein by reference.

In an alternative but less preferred embodiment of the invention multiple L1 proteins may be expressed within the same cell, from one or more DNA constructs. For example, multiple DNA constructs may be transformed or transfected into host cells, each vector encoding a different L1 protein. Alternatively a single vector having multiple L1 genes controlled by a shared promoter, or by multiple individual promoters, may be used. IRES elements may also be incorporated into the vector, where appropriate. Using such strategies the L1 proteins may be co-expressed and optionally co-purified for subsequent mixed VLP formation, or may spontaneously form mixed VLPs which can then be further purified. Preferably co-expression is carried out in an insect cell line. Preferably co-expression is of the L1 protein only. Preferably co-expression of different L1 species within the same cell allows for the L1 proteins from different HPV genotypes to be separably isolated.

The invention also relates to a vaccine comprising a mixed VLP as herein described. Vaccines may comprise a mixed VLP in combination with other mixed VLPS, single VLPs or other antigens. Additional antigens may, for example, be fused to L1 component of a VLP, encapsulated within the VLP or otherwise co-formulated or co-delivered with the VLP.

By way of example, the vaccine may comprise an HPV L2 protein or L2 derivative such as an L2 peptide, for example as disclosed in K. Kawana et al Vaccine 19, (2001) p1496–1502, incorporated herein by reference. In a further preferred embodiment the vaccine of the invention may be formulated with HPV early antigens such as E1, E2, E3, E4, E5, E6,E7, E8 or immunologically active derivatives thereof. When delivered in chimaeric form it is preferable to utilise an immunogenic fragment of about 30–60 amino acids of the early antigen. Early proteins may have the wild type sequence or comprise suitable mutations, for example, to prevent transforming activity.

The vaccine may be formulated or co-administered with non-HPV antigens. Suitably these antigens can provide protection against other diseases, most preferably sexually transmitted diseases such as herpes simplex virus, chlamydia and HIV. We particularly prefer that the vaccine comprise the gD protein or a truncate thereof from HSV. Preferably the antigen is the gD2t protein as described in WO 99/45957. In this way the vaccine provides protection against both HPV and HSV. Preferred HIV antigens are described in WO/9916884 and WO/0154719.

The vaccines of the invention may also comprise adjuvants in combination with the VLPs. Suitably the VLPs of the invention are used in combination with aluminium, and are suitably adsorbed or partially adsorbed onto aluminium adjuvants. Also preferred are adjuvants which stimulate a Th1 type response such as 3DMPL or QS21. Suitably the adjuvant is an aluminium salt, preferably in combination with 3D MPL, such as aluminium phosphate and 3D MPL. Aluminium hydroxide, suitably in combination with 3D MPL is also preferred.

When VLPs are adsorbed on to aluminium containing adjuvants, the adjuvant is preferably added before mixing of the VLPs to form the final vaccine product.

The vaccine may also comprise aluminium or an aluminium compound as a stabiliser.

The vaccines of the invention may be provided by any of a variety of routes such as oral, topical, subcutaneous, musosal (typically intravaginal), intraveneous, intramuscular, intranasal, sublingual, intradermal and via suppository. Intramuscular and intraderamal delivery are preferred.

The dosage of mixed VLP will vary with the condition, sex, age and weight of the individual, the administration route and type of PV of the vaccine. Suitably the delivery is of a therapeutic amount of VLP, suitable to generate an immunologically protective response. Suitably each vaccine dose comprises 1–100 μg of each mixed VLP, preferably 20–80 μg, preferably 40 μg of each mixed VLP. Preferably each vaccine comprises 1–50 μg of each protein, preferably 5–30 μg and most preferably 5 μg, 6 μg, 10 μg, 15 μg or 20 μg of each protein.

Suitably the vaccine is given in a 2 or 3 dose strategy, such as a 0, 6 dosing regime or a 0, 1 and 6 months. Suitably the vaccination regime incorporates a booster injection after 5–10 years, preferably 10 years.

Preferably the vaccine is a liquid vaccine formulation, although the vaccine may be lyophilised and reconstituted prior to administration.

Preferably the vaccine is used to vaccinate adolescents, preferably between 10–13 years of age.

Suitably the mixed VLPs of the invention can induce a protective immune response to at least one HPV type represented in the mixed VLP, and preferably to two or all of the HPV types represented.

The present invention is illustrated by the following Examples and Figures which are not limiting upon the invention, wherein:

FIG. 1 illustrates mixed VLPs in comparison with HPV 16 VLPs as assessed by EM; and FIGS. 2 and 3 illustrate size distribution of mixed VLPs.

EXAMPLE 1

A Preparation of HPV 16/18 L1 VLPs

Production of HPV 16 and HPV 18 VLPs was carried out using standard protocols—for example, see WO9913056. HPV 16/18 proteins were expressed in *Trichoplusia ni* (High Five™) cells (at a density of 350000 cells/ml) infected with recombinant Baculovirus (MOI of 0.3) encoding the HPV 16 or 18 L1 gene of interest. Cells were harvested approximately 72 hours post infection.

B Cell Harvest/Antigen Extraction

The antigen (L1-16/18) was extracted from Hi5 cells in a three step process of concentration, extraction, clarification. The concentration step consists removes up to 90% of the culture medium, and was performed by tangential flow filtration. The extraction step was performed with a hypotonic buffer (Tris 20 mM, pH 8.5). A volume equal to the culture volume was used to perform the extraction. A contact time of minimum half an hour under smooth agitation was used. The clarification was performed by tangential flow filtration.

C Purification

The purification process was carried out at room temperature. β-mercaptoethanol (4% w/w) was added to the extract in order to disassemble the VLP's into capsomers, for both antigens, L1-16/18. Glycerol was added up to a concentration of w/w 10% just prior to the addition of β-mercaptoethanol.

All buffers used were filtered on 0.221 μm filters prior to storage at 2° C.–8° C. Prior to each purification run, gel matrixes are sanitised and equilibrated with appropriate buffer before sample loading.

Purification regimes are given for the separate purification of L1 from both HPV 16 and 18. These schemes are broadly similar, and involve the steps of:

Anion exchange chromatography (Di methyl amino ethyl—DMAE),

Anion exchange chromatography (tri methyl amino ethyl—TMAE),

Hydroxyapatite chromatography,

Nanometric filtration (Planova),

Ultrafiltration,

Hydrophobic interaction chromatography (using Octyl Sepharose) for HPV 18 or

Anion exchange chromatography (DEAE) for HPV 16; and

Sterile filtration.

Specifically:

C1 Purification of L1-18 Antigen

Anion Exchange Chromatography DMAE

The clarified extract (protein at a concentration of ~1 g/ml, with the L1 protein at ~150 mg/ml) is applied to an anion exchange column (Di Methyl Amino Ethyl). Elution is performed with (Tris 20 mM|NaCl 200 mM|4% β-mercaptoethanol BME) buffer, pH 7.9±0.2. The antigen is eluted in approximately S column volumes and the elution profile is monitored at 280 nm.

Anion Exchange Chromatography TMAE

The eluate of the first step is diluted with 1 volume of $H_2O$/1ME 4%. The diluted eluate is then applied to a second anion exchange column (Tri Methyl Amino Ethyl). Elution is performed with (20 mM Tris|NaCl 200 mM|4% BME) buffer, pH 7.9±0.2. The antigen is eluted in approximately 4 column volumes and the elution profile is monitored at 280 nm.

Hydroxyapatite Chromatography

The eluate of the TMAE step is applied to a hydroxyapatite (HA) column. After sample application, the gel is eluted with approximately 2.5 column volumes of ($NaH_2PO_4$ 100 mM|NaCl 30 mM|4% BME) buffer, pH 6.0±0.2.

Nanometric Filtration (Planova)

The HA eluate is diluted in order to reach the following conditions: ($NaH_2PO_4$ 25 mM|NaCl 10mM|4% BME) buffer, pH 7.5±0.2.

Then it is filtered successively on a 0.2 μm prefilter and on a Planova 15N filter of 0.12 m². The filtration is performed at constant pressure 200 mbar±20 mbar.

Ultrafiltration

The ultrafiltration is performed with a tangential flow ultrafiltration system equipped with polyethersulfone membranes (Centramate cassette 0.1 m², 100 kD). The Planova eluate is treated to reach the following conditions: ($NaH_2PO_4$ 100 mM|NaCl 30 mM|4% BME), pH 6.0±0.2; then it is loaded in the system, concentrated 5 fold and dia-filtrated with continuous injection of –10 starting volumes of (NaH2PO4 20 mM|NaCl 500 mM) buffer, pH 6.0±0.2.

Hydrophobic Interaction Chromatography (Octyl Sepharose)

The ultrafiltration permeate is applied to an Octyl Sepharose column. This chromatography step is run in the negative mode with approximately 5 column volumes of ($Na_3PO_4$ 20 mM|NaCl 500 mM) buffer, pH 6.0±0.2.

Sterile Filtration

The purified L1-18 antigen solution is sterilised by filtration on a 0.22 μm membrane.

C2 Purification of L1-16 Antigen

Anion Exchange Chromatography DMAE

The clarified extract is applied to an anion exchange column (Di Methyl Amino Ethyl). Elution is performed with (Tris 20 mM|NaCl 180 mM|4% BME) buffer, pH 7.9±0.2. The antigen is eluted in approximately 4 column volumes and the elution profile is monitored at 280 nm.

Anion Exchange Chromatography TMAE

The eluate of the first step is diluted with 1 volume of $H_2O$/BME 4%. The diluted eluate is then applied to a second anion exchange column (Tri Methyl Amino Ethyl). Elution is performed with (20 mM Tris|NaCl 180 mM|4% BME) buffer, pH 7.9±0.2. The antigen is eluted in approximately 5 column volumes and the elution profile is monitored at 280 nm.

Hydroxyapatite Chromatography (EIA)

The eluate of the TMAE step is applied to a HA column. After sample application, the gel is eluted with approximately 3 column volumes of ($NaH_2PO_4$ 100 mM|NaCl 30 mM|4% BME) buffer, pH 6.0±0.2.

Nanometric Filtration (Planova)

The HA eluate is diluted in order to reach the following conditions: ($NaH_2PO_4$ 25 mM|NaCl 10 mM|4% BME) buffer, pH 7.5±0.2. Then it is filtered successively on a 0.2 μm prefilter and on a Planova 15N filter of 0.12 m². The filtration is performed at constant pressure 200 mbar±20 mbar.

Ultrafiltration

The ultrafiltration is performed with a tangential flow ultrafiltration system equipped with polyethersulfone membranes (Centramate cassette 0.1 m², 100 kD). The Planova eluate is treated to reach the following conditions: ($NaH_2PO_4$ 100 mM|NaCl 30 mM|4% BME), pH 6.0±0.2; then it is loaded in the system, concentrated 5 fold and dia-filtrated with continuous injection of –10 starting volumes of ($NaH_2PO_4$ 20 mM|NaCl 500 mM) buffer, pH 6.0±0.2.

Anion Exchange Chromatography DEAE

The ultrafiltration eluate is adjusted to the conductivity of the equilibrium buffer, ($Na_3PO_4$ 20 mM|NaCl 250 mM), pH 6.0±0.2 and applied on an anion exchange column (Di Ethyl Amino Ethyl). Elution is performed with ($NaH_2PO_4$ 20 mM|NaCl 500mM) buffer, pH 6.0±0.2. The antigen is eluted in approximately 3 column volumes and the elution profile is monitored at 280 nm.

Sterile Filtration

The purified L1-16 antigen solution is sterilised by filtration on a 0.22 μm membrane.

D Formation of Mixed VLPs

The process of the invention involves combining the HPV 16 and 18 L1 proteins, capsomers to permit the formation of a mixed VLP. HPV 16 and 18 L1 components may be combined at any suitable point in the above process prior to the point at which the VLPs are reassembled. Where necessary, if L1 VLPS have already formed, then these can be disassembled and reassembled to form the mixed VLP.

By way of example 2 specific strategies have been tested:

1 mixing of both antigens after the HA step. Based on the L1 concentration in HA pools, the two components are mixed to reach an equal concentration of HPV16 and 18 to start the UF step. In this case after the ultrafiltration step an Octyl speharose step is performed as for HPV 18 purification followed by a DEAE step as performed in the HPV 16 procedure.

2 mixing of both extracts and copurify. Based on the L1 concentration in Extracts, the two valences are mixed to reach an equal concentration of HPV16 and 18 to start the DMAE step. Again, after the ultrafiltration step an Octyl speharose step is performed as for HPV 18 followed by a DEAE step as performed in the HPV 16 procedure.

HPV16-HPV18 VLP-Mixed at UF Step

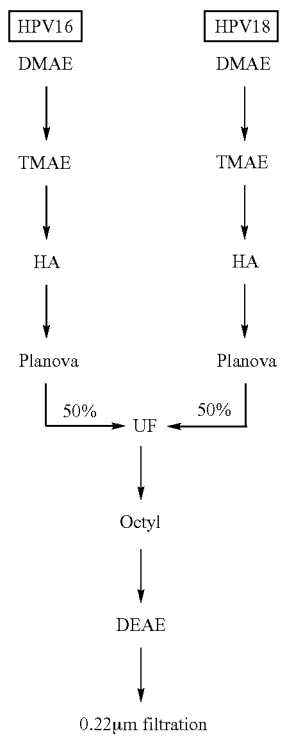

HPV16-HPV18 VLP-Mixed at DMAE Step

The same flow sheet is applied but the mixing is performed at the DMAE step instead of the UF step. The concentration used for elution at the anion exchange DMAE TMAE steps is 200 mM.

Results

HPV16-HPV18 VLP-Mixed at UF Step 2 lots of mixed VLPs (lot numbers 31 b165c and 31b166c) were produced by combining HPV 16 and BPV 18 L1 proteins.

Purity by SDS-Page

The purity of the mixed VLP's was as good as both "classical" HPV 16 or HPV 18 bulks. The purity of the bulks was higher than 95%.

EM data—FIG. 1

The EM of 31B165C (UF Retentate after maturation) was compared to a classical HPV16 lot (39B122c). VLP's were well formed, homogeneous in size, without aggregation; some ribbons of capsomeres are present in both experiments.

Size Distribution

The size distribution of the VLP's were determined using a Malvern Zetasizer 3000 HS.

The samples were measured undiluted into a plastic cuvette for Malvern analysis (800 μl/cuvette).

The technical conditions were:
laser wavelength: 532 nm,
laser power: 50 mW,
scattered light detected at 90°,
temperature: 25° C.,
duration: automatic determination by the software,
number: 3 consecutive measurements,
z-average diameter: by cumulants analysis,
size distribution: by the Contin method.

Classical results for HPV18 L1-VLP's are: 70–80 nm with good polydispersity (<0.1)

Classical results for HPV16 L1-VLP's are: 60–70 nm with good polydispersity (<0.1)

For mixed VLP's, the following results were obtained:
31 B165c: 85 nm with good polydispersity (0.08). VLP's are almost completely formed at the beginning of maturation
31 B166c: 76 nm with good polydispersity (0.08).

The size distribution of lot 31 B165c and 31 B166c as measured by dynamic laser light scattering are shown in FIGS. 2 and 3.

HPV16-HPV18 VLP Mixed at DMAE Step

Lot n°. 31B167B was made up from lots E18L1C005 (BPV18) and 39B167 (HPV16).

Purity by SDS-Page

The purity of the mixed VLP's was as good as both "classical" bulks.

The purity of the bulks was higher than 95%.

Size Distribution

The size distribution of the VLP's were determined by using a Malvern Zetasizer 3000 HS as above.

Classical results for HPV18 L1-VLP's are: 70–80 nm with good polydispersity (<0.1)

Classical results for HPV16 L1-VLP's are: 60–70 nm with good polydispersity (<0.1)

For mixed VLP's, the following results were obtained:
HPV16-HPV18 31B167B: 74 nm with good polydispersity (0.07). VLP's were almost completely formed at the beginning of maturation.

E

Where appropriate the mixed VLPs may be adsorbed onto an aluminium salt, as follows:

60 μg of purified VLPs are adsorbed on 150 μg $Al^{3+}$ from $Al(OH)_3$, at a pH of 6.0±0.2, for one hour at room temperature with gentle stirring. This concentrated adsorbed monovalent is stored at +4° C. Adsorption is checked by centrifuging the preparation and quantifying VLPs in the supernatant.

The invention claimed is:

1. A process for the production of a mixed VLP, the process comprising the steps of:
  (a) expression of an L1 protein or functional protein derivative from one papillomavirus;
  (b) expression of an L1 protein or functional protein derivative from a second papillomavirus, wherein steps (a) and (b) are carried out separately; and
(c) mixing of the expressed proteins wherein the process results in the formation of a mixed VLP comprising L1 proteins from at least 2 different types of human papillomavirus.

2. A process according to claim 1 wherein the proteins are subject to a purification step before being mixed in step (c).

3. A process according to claim 1 wherein the proteins are purified after VLP assembly.

4. A process according to claim 1 wherein the L1 proteins or functional protein derivatives expressed in steps (a) and (b) are contacted by a reducing agent, and the mixing of proteins in step (c) takes place prior to removal of the reducing agent from the mixture of proteins.

5. A process according to claim 4 wherein the reducing agent is β-mercaptoethanol.

6. A mixed VLP obtained or obtainable by a process according to claim 1 wherein the mixed VLP comprises an HPVI16 L1 protein or functional protein derivative and an HPVI 18 L1 protein or functional protein derivative.

7. A mixed VLP according to claim 6 wherein the L1 proteins in the VLPs are not in the form of a fusion protein with another L1 protein or part of an L1 protein.

8. A mixed VLP according to claim 6 comprising L1 proteins from only 2 L1 genotypes.

9. A mixed VLP according to claim 6 wherein at least one L1 protein is truncated.

10. A mixed VLP according to claim 6 wherein the mixed VLP further comprises an L1 protein or functional L1 protein derivative from HPV genotypes selected from the list group consisting of 1, 2, 3, 4, 5, 6, 7, 8, 9, 11, 12, 14, 15, 16, 17, 18, 19, 20, 21, 22, 23, 24, 25, 26, 27, 28, 29, 31, 33, 34, 35, 36, 37, 38, 39, 42, 43, 44, 45, 51, 52, 56, 58, 59, 66, 68 and 73.

11. The process according to claim 1 wherein at least one L1 protein or functional L1 protein derivative is from HPV 16.

12. The process according to claim 1 wherein at least one L1 protein or functional L1 protein derivative is from HPV 18.

13. A mixed VLP according to claim 6 wherein the polydispersity of the mixed VLP preparation is less than 0.15 as measured using a Malvern Zetasizer 3000 HS under the conditions of:
laser wavelength: 532 nm,
laser power: 50 mW,
scattered light detected at 90°,
temperature: 25° C.

14. A mixed VLP according to claim 6 additionally comprising an HPV L2 antigen or functional derivative thereof.

15. A mixed VLP according to claim 6 additionally comprising an HPV early antigen or functional derivative thereof.

16. A vaccine comprising the mixed VLP according to claim 6.

17. A vaccine according to claim 16 additionally comprising another antigen, VLP or mixed VLP.

18. A vaccine according to claim 17 wherein the antigen is derived from an organism capable of causing a sexually transmitted disease.

19. The vaccine according to claim 16, additionally comprising an adjuvant.

20. The vaccine according to claim 19 wherein the adjuvant comprises an aluminium salt.

21. The vaccine according to claim 20 wherein the adjuvant is aluminium hydroxide and 3D-MPL.

22. A method of treatment of an individual at risk from, or suffering from, a disease related to papillomavirus infection comprising treatment of the individual with an effective amount of a vaccine according to.

* * * * *